United States Patent [19]

Eberhardt et al.

[11] Patent Number: 5,716,401
[45] Date of Patent: Feb. 10, 1998

[54] HOLDER FOR HEART VALVE

[75] Inventors: Carol E. Eberhardt, Fullerton; David J. Myers, Garden Grove, both of Calif.; Robert A. Pinkul, Phoenix, Ariz.

[73] Assignee: Medtronic, Inc., Minneapolis, Minn.

[21] Appl. No.: 566,446

[22] Filed: Dec. 1, 1995

Related U.S. Application Data

[62] Division of Ser. No. 230,658, Apr. 21, 1994, Pat. No. 5,476,510.

[51] Int. Cl.⁶ .................................................. A61F 2/24
[52] U.S. Cl. ........................... 623/2; 623/900; 606/99
[58] Field of Search .................... 623/2, 66, 900; 606/1, 99

[56]  References Cited

U.S. PATENT DOCUMENTS

| | | | |
|---|---|---|---|
| 893,055 | 7/1908 | Conner | 606/127 |
| 3,409,013 | 11/1968 | Berry | 623/2 |
| 3,828,787 | 8/1974 | Anderson et al. | 623/2 |
| 3,996,623 | 12/1976 | Kaster | 623/2 |
| 4,056,853 | 11/1977 | Boretos et al. | 623/2 |
| 4,106,129 | 8/1978 | Carpentier | |
| 4,585,453 | 4/1986 | Martin | 623/2 |
| 4,655,218 | 4/1987 | Kulik | 128/321 |
| 4,679,556 | 7/1987 | Lubock | 128/303 R |
| 4,683,883 | 8/1987 | Martin | 128/303 R |
| 4,801,015 | 1/1989 | Lubock | 206/438 |
| 4,865,600 | 9/1989 | Carpentier | 623/2 |
| 4,990,151 | 2/1991 | Wallsten | 606/108 |
| 5,026,377 | 6/1991 | Burton et al. | 606/108 |
| 5,037,434 | 8/1991 | Lane | 623/2 |
| 5,074,858 | 12/1991 | Ramos Martinez | 606/1 |
| 5,089,015 | 2/1992 | Ross | 623/2 |
| 5,236,450 | 8/1993 | Scott | 623/2 |
| 5,443,502 | 8/1995 | Caudillo et al. | 623/2 |
| 5,476,510 | 12/1995 | Eberhardt et al. | 623/2 |
| 5,480,425 | 1/1996 | Ogilive | 623/2 |

FOREIGN PATENT DOCUMENTS

| | | |
|---|---|---|
| 0207339 | 12/1967 | U.S.S.R. |
| 878285 | 11/1981 | U.S.S.R. |
| 1008937 | 7/1984 | U.S.S.R. |
| 1149969 | 4/1985 | U.S.S.R. |
| 1264923 | 10/1986 | U.S.S.R. |
| 1507368 | 9/1989 | U.S.S.R. |
| 1621912 | 1/1991 | U.S.S.R. |
| 1690738 | 11/1991 | U.S.S.R. |
| 1690739 | 11/1991 | U.S.S.R. |
| 0005255 | of 1825 | United Kingdom |
| 9200399 | 3/1992 | WIPO |
| 9212688 | 8/1992 | WIPO |

*Primary Examiner*—John G. Weiss
*Assistant Examiner*—Bruce E. Snow
*Attorney, Agent, or Firm*—Harold R. Patton; Curtis D. Kinghorn; Peter Forrest

[57]  ABSTRACT

A holder for a prosthetic heart valve is disclosed. The holder, comprising a holder assembly disposed at the distal end of an elongate handle, includes a plurality of distally-projecting fingers adapted to engage the commissure posts of a stented prosthetic valve. The commissure-engaging fingers are movable in a radially-inward direction toward the longitudinal axis of the holder. A mechanism is provided for retaining the fingers in an inwardly-moved position. When the commissure posts of the valve are coupled to the fingers, inward movement of the fingers causes the commissure posts to be deflected inward with respect to the valve, improving the implanting surgeon's access to the valve's suture ring and surrounding tissue.

4 Claims, 8 Drawing Sheets

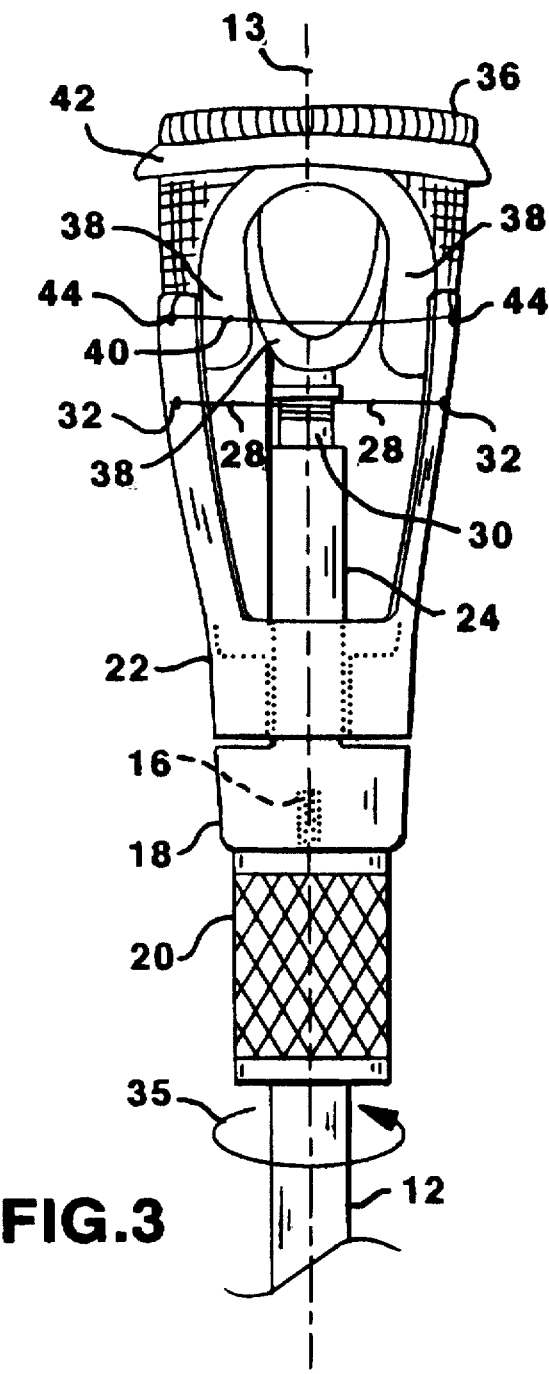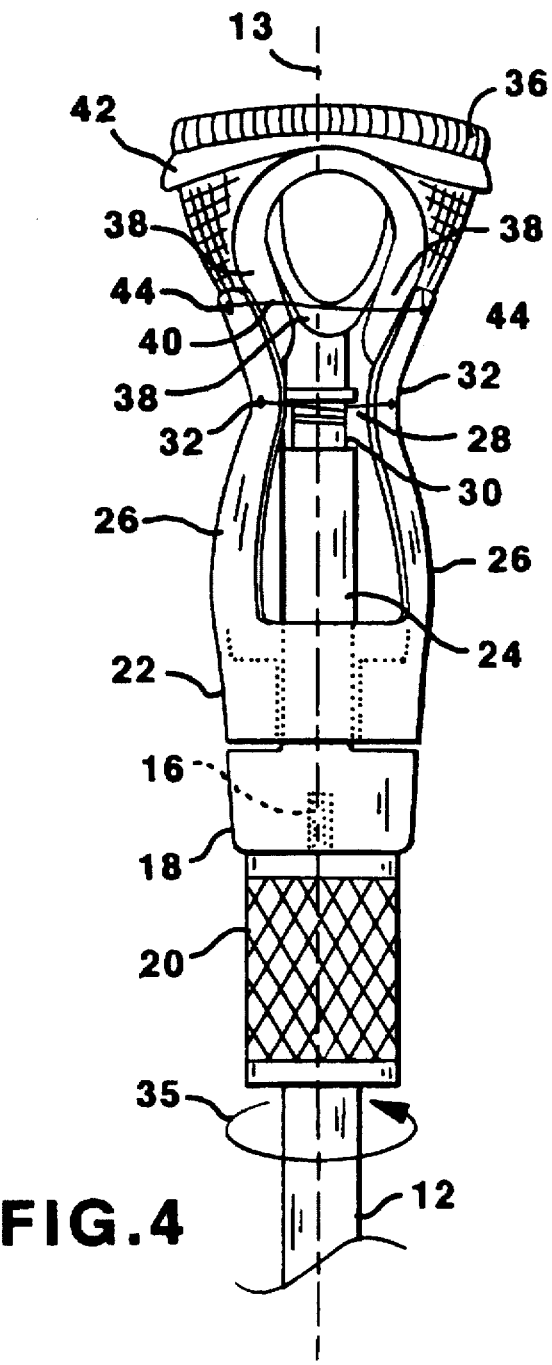

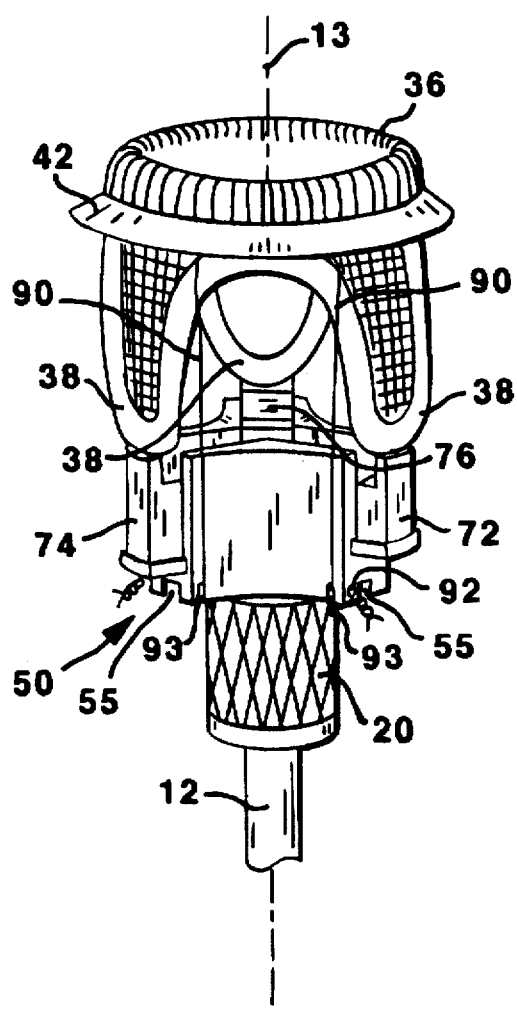 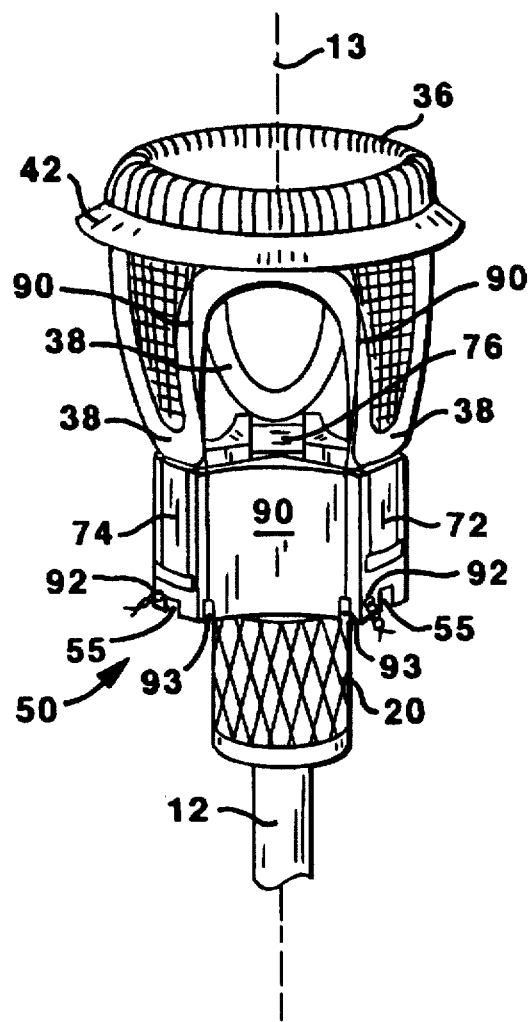
FIG. 13  FIG. 14

5,716,401

HOLDER FOR HEART VALVE

This is a divisional of application Ser. No. 08/230,658 filed on Apr. 21, 1994 now U.S. Pat. No. 5,476,510.

FIELD OF THE INVENTION

This invention relates generally to the field of implantable valvular prostheses, and more particularly to a holding mechanism used for implantation of valvular prostheses.

BACKGROUND OF THE INVENTION

Various types and configurations of prosthetic heart valves, used to replace diseased natural human heart valves, are known in the prior art.

Prosthetic heart valves, at least those which include valve leaflets, can be generally categorized into one of two basic classes of replacement heart valves. The first class includes heart valves which have one or more relatively rigid leaflets formed of a stiff biocompatible material. The second class includes what will be referred to in this disclosure as bioprosthetic valves, which have flexible leaflets, typically made of a biological material. Among the known bioprosthetic valves, there are those which have a semi-rigid or relatively flexible frame or stent with (typically) three leaflets attached thereto, and those which have no stent. The stent in a stented replacement heart valve typically defines a substantially circular base of the valve body, around which an annular suture ring is disposed for suturing the valve to surrounding tissue, and further comprises commissure posts defining the juncture between adjacent leaflets.

Examples of bioprosthetic valves are described in U.S. Pat. No. 4,106,129 to Carpentier et al., entitled "Supported Bioprosthetic Heart Valve with Compliant Orifice Ring," and in U.S. Pat. No. 5,037,434 to Lane, entitled "Bioprosthetic Heart Valve with Elastic Commissures." The Carpentier et al. '129 patent describes a stent comprising a frame composed of a single flexible wire preformed to define a generally circular base which is interrupted at circumferentially-spaced points by three inverted U-shaped commissure posts which project generally normally with respect to the circular base. The Lane '434 patent describes a stent composed of a flexible metal ribbon similarly preformed to define three commissure posts which project generally normally with respect to a generally circular base. (This generally normally-projecting commissure support configuration exemplified by the Carpentier et al. '129 and Lane '434 patents is well-known in the art, and has alternatively been characterized in the prior art as comprising "axially-projecting" or "upwardly projecting" commissure supports.)

Both the Lane '434 and Carpentier et al. '129 patents describe a conventional configuration of three leaflets, wherein one leaflet is disposed between each pair of commissure posts.

The Hancock® Modified Orifice Aortic Bioprosthesis and the Hancock® M.O. II Bioprosthesis, manufactured by Medtronic, Inc., Minneapolis, Minn., are commercially-available examples of bioprosthetic valves. The Hancock® Modified Orifice Bioprosthesis, available since 1976, and the Hancock® M.O. II, available since 1978 are both available in various sizes, for example, 19-, 21-, 23-, and 25-mm, such that they may be implanted in patients having correspondingly varying sizes of aortic annuli.

To facilitate the implantation of heart valve prostheses, various types of specialized holders have been developed. Such holders are intended to enable the implanting surgeon to precisely position the heart valve and suture ring either within the heart passageway or adjacent/above the aortic root of the patient and to securely hold the valve assembly in place until suturing is complete and the sutures are tied off.

Various prosthetic valve holders have been proposed in the prior art, including those discussed in U.S. Pat. No. 4,585,453 to Martin et al., entitled "Disposable Holder for Prosthetic Heart Valve," in U.S. Pat. No. 4,655,218 to Kulik et al., entitled "Prosthetic Valve Holder," in U.S. Pat. No. 4,679,556 to Lubock et al., entitled "Releasable Holder and Method of Use," in U.S. Pat. No. 4,683,883 to Martin, entitled "Two-Piece Heart Valve Holder/Rotator," in U.S. Pat. No. 4,801,015 to Lubock et al., entitled "Releasable Holder and Package Assembly for a Prosthetic Heart Valve," and in U.S. Pat. No. 4,865,600 to Carpentier et al., entitled "Mitral Valve Holder."

One problem which has been encountered during aortic valve replacement is that the laterally and upwardly projecting commissure posts can obstruct the surgeon's access to the valve base, making suturing of the suture ring to surrounding tissue and tying-off of the implanting sutures difficult. Such problems are particularly evident in patients having a relatively small aortic root.

SUMMARY OF THE INVENTION

The present invention is directed toward alleviating the problems associated with implantation of replacement heart valves, and in particular, the replacement of aortic valves, especially small diameter ones.

In particular, and in accordance with one aspect of the present invention, there is provided a holder which facilitates implantation of prosthetic aortic valves, and which further functions to deflect the valve's commissure posts generally inwardly during the implantation procedure, improving the surgeon's access to the suture ring and host tissue disposed around the base of the replacement valve.

In accordance with one embodiment of the invention, a holder is provided with a plurality of distally-projecting fingers adapted to engage the commissure posts of a prosthetic valve. The fingers are movable inwardly, i.e., toward the longitudinal axis of the holder, such that the commissure posts are deflected inwardly with respect to the valve.

In accordance with another aspect of the invention, the commissure-engaging fingers are provided with a mechanism for preventing outward movement thereof once they have been moved inward, such that the commissure posts remain in their deflected position during the implant procedure.

In one disclosed embodiment, the mechanism for achieving inward deflection of the valve's commissure posts includes a rotating central shaft disposed centrally with respect to the distally-projecting fingers of the holder. Each of the fingers is coupled to the central shaft via a connecting line, such that rotation of the central shaft results in the connecting lines being wrapped around the central shaft. This causes each of the fingers to be drawn inward.

In another disclosed embodiment, a holder is provided with distally-projecting fingers which are slidably mounted in the holder main body. Each of the fingers is movable inwardly toward the longitudinal axis of the holder. Sawtooth detents on the slidably-mounted fingers resist outward moving of the fingers away from the longitudinal axis of the holder, so that the commissure posts coupled to the fingers are maintained in a deflected position during an implant procedure.

BRIEF DESCRIPTION OF THE DRAWINGS

The above-described and other aspects of the present invention may be better understood and appreciated with reference to a detailed description of specific embodiments of the invention, when read in conjunction with the accompanying drawings, wherein:

FIG. 3 is a side view of the valve holder from FIG. 1 with a prosthetic valve mounted thereon;

FIG. 4 is a side view of the valve holder from FIG. 1 with a prosthetic valve mounted thereon and with its distally-projecting fingers having been drawn in toward the longitudinal axis of the holder;

FIG. 13 is a side view of the holder from FIG. 6 having a prosthetic valve mounted thereon; and FIG. 14 is a side view of the holder and valve from FIG. 13 with the commissure posts of the valve deflected inwardly.

DETAILED DESCRIPTION OF SPECIFIC EMBODIMENTS OF THE INVENTION

Figure 1:
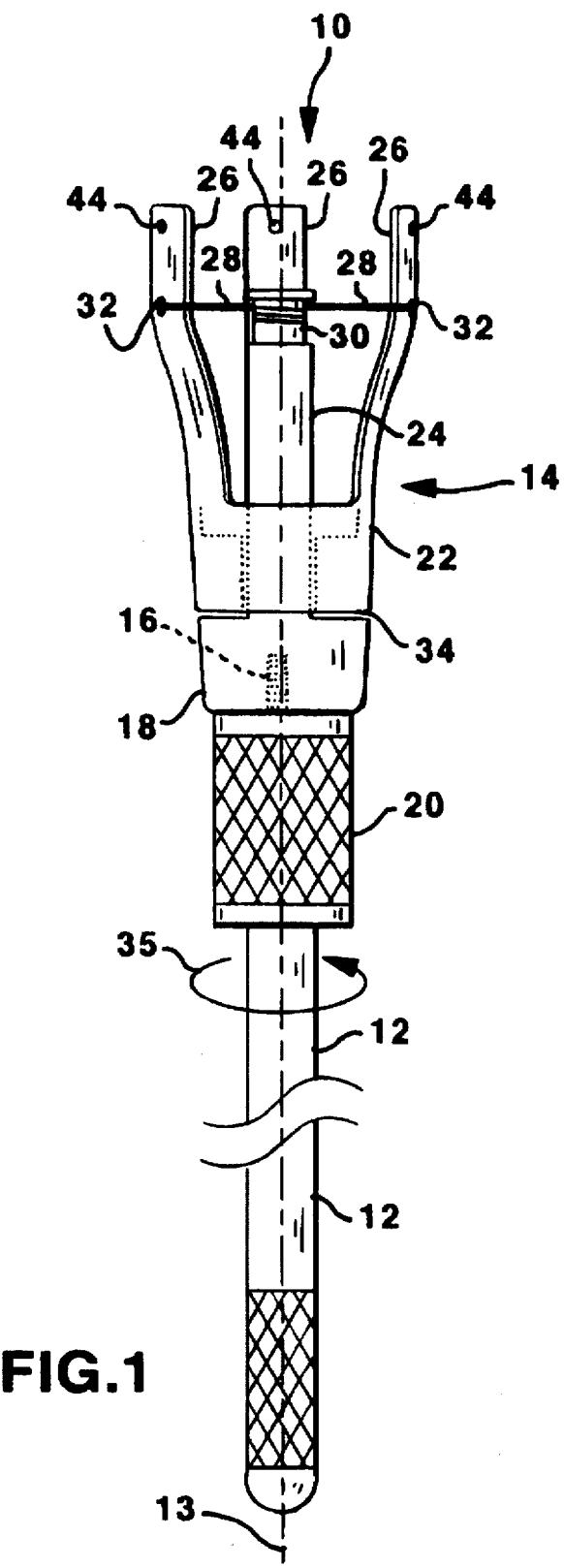
FIG. 1 is a side view of a prosthetic valve holder in accordance with one embodiment of the invention.

Referring to FIG. 1, there is shown a prosthetic valve holder 10 in accordance with one embodiment of the present invention. Holder 10 comprises an elongate handle 12, which is preferably made of stainless steel or another suitably rigid, sterilizable material. Handle 12 defines a central, longitudinal axis 13 of holder 10. In the presently preferred embodiment, handle 12 is a Medtronic Model 0791 Pliant Handle, which is approximately 22-cm long and which has a reduced diameter portion along its length (not shown) for enabling the handle to be bent to a desired angle during the valve implant procedure.

A holder assembly in accordance with one embodiment of the invention, designated generally with reference numeral 14 in FIG. 1, is disposed at the distal end of handle 12. As shown in FIG. 1, holder assembly 14 is coupled to handle 12 by means of a threaded post 16 which is screwed into a rotor portion 18 of assembly 14. A knurled lock-nut 20 tightens against rotor portion 18 to securely and adjustably affix holder assembly 14 to handle 12.

Rotor portion 18 of holder assembly 14 is rotatably coupled to a stator portion 22. In the presently disclosed embodiment of the invention, this rotational coupling is accomplished through providing a central stem 24, integral with rotor portion 18, which projects distally from rotor portion 18 and extends axially through stator portion 22, thereby forming the axis of the rotational connection between rotor portion 18 and stator portion 22. In the presently preferred embodiment of the invention, rotor portion 18 and stator portion 22 are made of sterilizable, injection-molded plastic.

Peripherally spaced around, and extending generally distally from stator portion 22 are a plurality of fingers 26. In the presently preferred embodiment of the invention, there are three such fingers 26, corresponding to the number of commissure posts on conventional tricuspid prosthetic valves, although it is to be understood that more or fewer fingers 26 could be provided depending upon the valve configuration of a given application of the present invention. Fingers 26 are preferably somewhat compliant, such that they may each be drawn radially inward toward longitudinal axis 13, as will hereinafter be described in greater detail.

With continued reference to FIG. 1, associated with each finger 26 is a connecting line 28, each connecting line 28 being coupled at one end to an associated finger 26 and at another end to the distal end of central stem 24, within a groove or recess 30 formed therein. In the presently disclosed embodiment, connecting lines 28 are made of a conventional suture material. Holes 32 in fingers 26 allow lines 28 to be tied to the respective fingers 26, and a hole (not shown) may be provided in central stem 24 for the same purpose.

Figure 2:
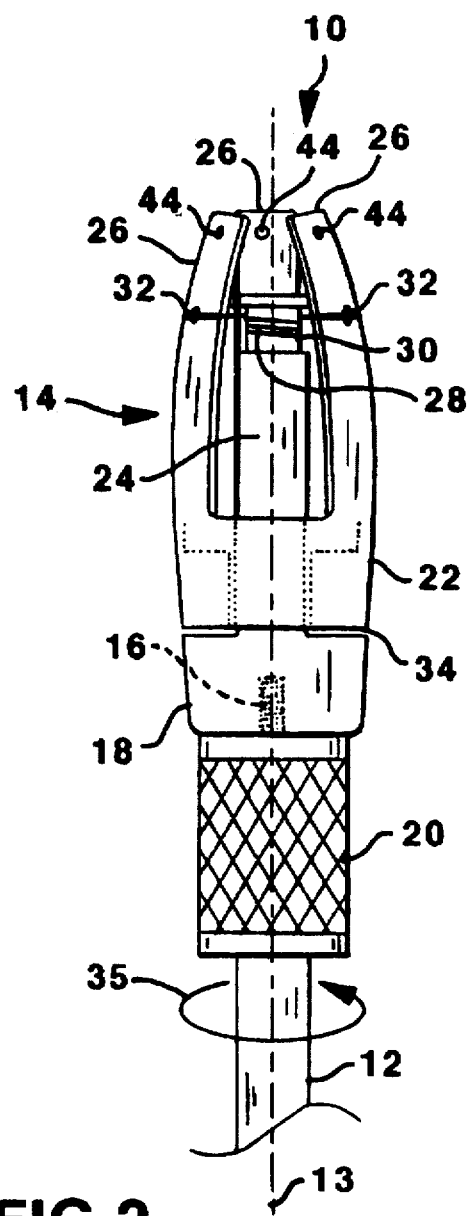
FIG. 2 is a side view of the valve holder from FIG. 1 with its distally-projecting fingers having been drawn in toward the longitudinal axis of the holder.

Referring now to FIGS. 1 and 2, it will be apparent to those of ordinary skill in the art that rotation of handle 12 in the direction of the arrow designated 35 in FIG. 1 (and the consequential rotation of rotor portion 18 and central stem 24) results connecting lines 28 being wrapped around central stem 24. As this occurs, fingers 26 are each drawn radially inward toward longitudinal axis 13, as previously mentioned, and as shown in FIG. 2.

In accordance with the presently disclosed embodiment of the invention, it is contemplated that fingers 26 may be maintained in the drawn-in position shown in FIG. 2 as a result of a frictional fit between rotor portion 18 and stator portion 22 of holder assembly 14. In particular, it is contemplated that rotor 18 and stator 22 may be configured such that force between those two elements is maintained in the area of their interface, designated as 34 in FIGS. 1 and 2. Alternatively, detents and corresponding grooves (not shown) may be provided on rotor 18 and stator 22 in the region of interface 34 to further enhance the frictional coupling between rotor 18 and stator 22, such that fingers 26 may be stably maintained in a drawn-in position.

The manner in which holder 10 is used to facilitate a prosthetic valve implantation procedure may be best appreciated with reference now to FIGS. 3 and 4, which each show holder 10 in relation to a prosthetic valve, designated with reference numeral 36. As shown in FIG. 3, valve 36 is installed in holder 10 with commissure posts designated with reference numeral 38 facing proximally with respect to handle 12. A suture ring 42 is provided around the generally circular base of valve 36, in accordance with the prior art. During the implantation procedure, valve 36 is maintained in holder 10 by means of a temporary suture 40, which is removed once suture ring 42 has been sutured to surrounding tissue in accordance with conventional surgical practice. Holes 44 provided near the distal tips of fingers 26 facilitate this temporary suturing of valve 36 into holder 10.

Preferably, suture 40 is a single, continuous thread which is affixed to holder 10, so that when suture 40 is cut by the surgeon following the suturing in place of valve 36, suture 40 is automatically extracted from valve 36 as holder 10 is withdrawn.

Figure 5:
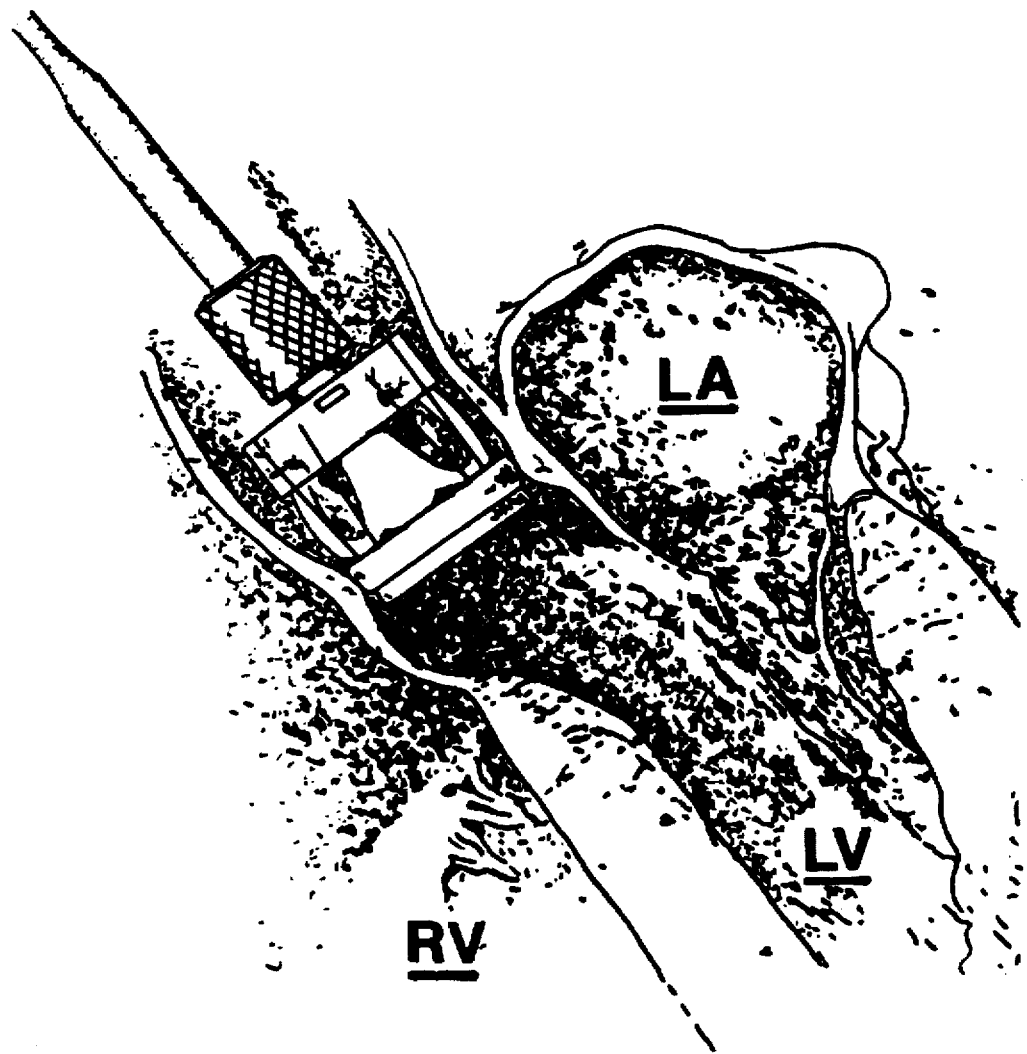
FIG. 5 is an illustration of a prior art valve holder being used during implantation of a valve in the aortic root of a patient.
Figure 7:
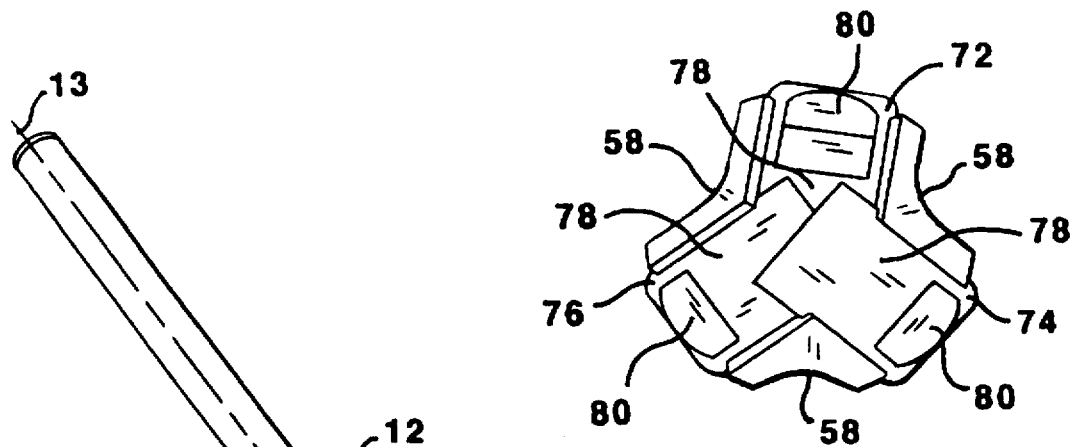
FIG. 7 is an end view of the holder from FIG. 6.

As previously noted, commissure posts 38 of valve 10 project generally normally with respect to the circular base of valve 36, when valve 10 is in a relaxed state. However, in such a state, commissure posts 38 tend to obstruct the surgeon's access to suture ring 42 and to surrounding tissue. This difficulty can perhaps be better appreciated with reference to FIG. 5, which shows valve 36 being positioned for implantation within the aortic root 46 of a patient using a conventional (prior art) valve holder 10'. It can be seen from FIG. 5 that in accordance with the prior art, commissure posts 38 are not deflected inwardly, leaving a minimal amount of space between posts 38 and the walls (annular tissue) of the aorta. This arrangement can complicate the implantation procedure, as the surgeon's access to suture ring 42 and the surrounding tissue is obstructed.

Returning to FIGS. 3 and 4, when handle 12 (and consequently, rotor portion 18 of holder assembly 14, and central stem 24) is rotated in the direction of arrow 35 to draw fingers 26 inward toward longitudinal axis 13 as previously described, commissure posts 38 are deflected inwardly as well, thereby improving the surgeon's access to suture ring 42 during suturing and implant. As previously noted, commissure posts 38 are maintained in this deflected position due to the frictional engagement of rotor 18 and stator 22 in the region of interface 34.

Usually, after implant, suture 40 is cut and holder 10 is withdrawn from the implant site, although the surgeon may choose to remove the valve from the holder 10 at any time prior to completion of the implant. When holder 10 is removed, commissure posts 38 return to their relaxed (undeflected) position.

Figure 6:
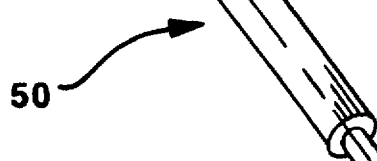
FIG. 6 is a perspective view of a valve holder in accordance with another embodiment of the present invention.

Turning now to FIG. 6, there is shown a prosthetic valve holder 50 in accordance with an alternative embodiment of the present invention. Holder 50 comprises a holder assembly 52 disposed at the distal end of elongate handle 12 used with the embodiment of the invention previously described with reference to FIGS. 1–4, handle 12 again defining a longitudinal axis 13 of holder 50. As with the previous embodiment, knurled lock nut 20 serves to secure holder assembly 52 to the distal end of handle 12.

Figure 8:
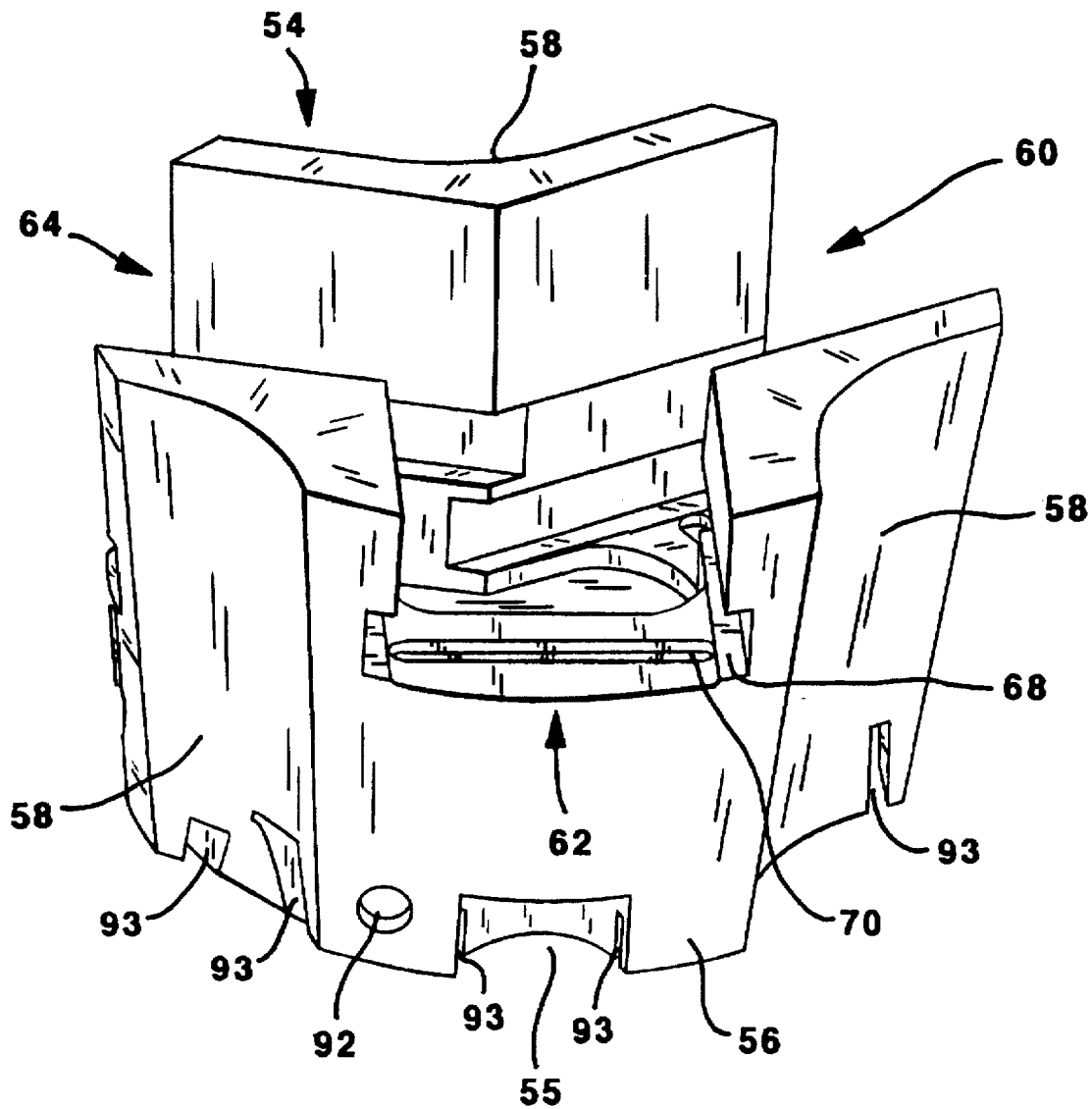
FIG. 8 is an enlarged perspective view of the main holder assembly body from the holder from FIG. 6.

Holder assembly 52 in the embodiment of FIGS. 6 through 14 comprises a main body portion 54 as best illustrated in FIG. 8. Main body portion 54 has a shape defined by three separate side facets, designated with reference numerals 56 in FIG. 6. Facets 56 are mutually spaced apart from one another and separated by generally arcuate portions 58, as can perhaps be better seen in the end view of holder assembly 52 shown in FIG. 7 and in the enlarged perspective view of main body portion 54 in FIG. 8.

With reference to FIG. 8, the configuration of main body portion 54 of holder assembly 52 is such that three channels 60, 62, and 64 are defined in the distal end thereof, each of said channels 60, 62, and 64 being generally associated with one of the facets 56 and extending from a facet 56 toward longitudinal axis 13 of holder 50. As shown in FIG. 8, channels 60, 62, and 64 each include a flared bottom portion 68. In addition, in the presently disclosed embodiment of the invention, each channel 60, 62, and 64 has an elongate groove 70 formed in the bottom therein, each groove oriented transversely to the length dimension of the channel in which it is formed. From FIG. 8 it can also be seen that channels 60, 62, and 64 each differ in depth, such that the depth of flared bottom portions 68 are different for each channel 60, 62, and 64.

Figure 9:
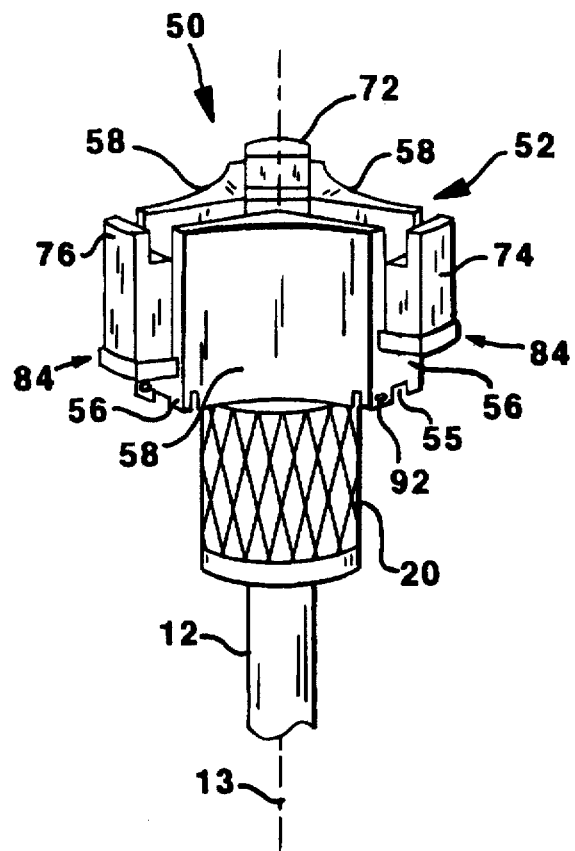
FIG. 9 is a perspective view of the holder assembly from the holder of FIG. 6.
Figure 12:
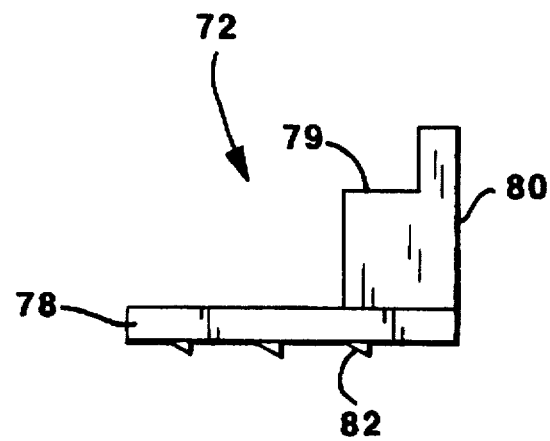
FIGS. 12 and 12A are enlarged side views of the engaging members from FIGS. 11 and 11A.
Figure 11A:
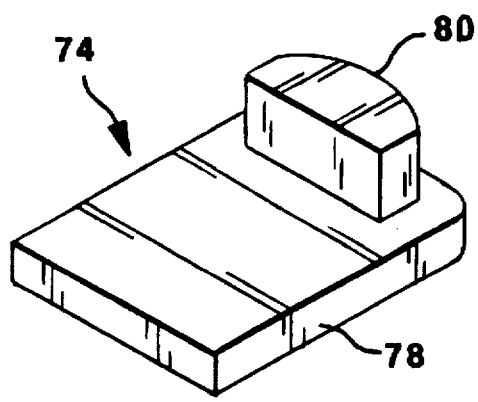
Figure 12A:
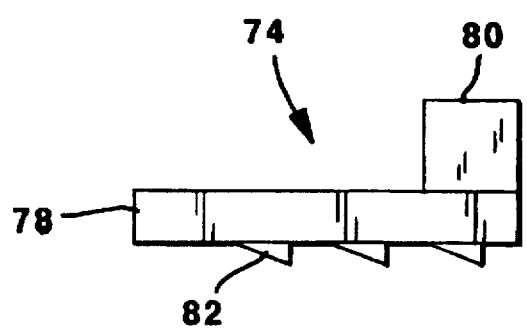

Referring now to FIG. 9, slidably disposed within each one of channels 60, 62, and 64 in main body portion 54 is an engaging member, identified with reference numerals 72, 74, and 76, respectively. An enlarged perspective view of engaging members 72 and 74 are provided in FIGS. 11 and 11A, and enlarged side views of engaging members 72 and 74 are shown in FIGS. 12 and 12A. Engaging member 72 includes a generally flat sliding base portion 78, and a finger portion 80 oriented perpendicularly with respect to sliding base portion 78. Finger portion 80 may include a step portion 79 to accommodate a different sized commissure post. Base portion 78 is wider than finger portion 80, such that when engaging member 72 is inserted into channel 62, base portion 78 engages flared bottom portion 68 of the channel, thereby securing engaging member 72 within the channel. The shape of engaging member 74 as seen in FIG. 11A is similar to that of engaging member 72, except that there is no step portion 79.

It should be understood that the shape and dimensions of finger portions 80 will depend on the size and shape of the replacement heart valve being implanted. Additionally, step portions 79 may be included on one or more of the engaging members.

With reference to FIGS. 12 and 12A, engaging members 72 and 74 have a plurality of saw-tooth detents 82 disposed thereon, oriented such that detents 82 engage groove 70 in the bottom of channel 62. The saw-tooth configuration of detents 82 is preferred since, as would be appreciated by those of ordinary skill in the art, such a configuration allows sliding of, for example, engaging member 74 in channel 62 radially inward toward longitudinal axis 13 of holder 50, while at the same time tends to resist sliding of engaging member 74 in the opposite, radially outward direction away from longitudinal axis 13.

The height of each engaging member's finger portion (e.g., finger portion 80 of engaging member 74) varies in accordance with the height of the channel 60, 62, or 64, with which each engaging member is associated. In this way, and as is apparent from FIG. 9, for example, the extreme distal tips of the finger portions 80 of each engaging member 72, 74, 76 project distally to a common extent. Alternatively, for some valves in which the three commissure posts are not all the same length, it may be desirable to vary the length of finger portions 80 accordingly.

Figure 10:
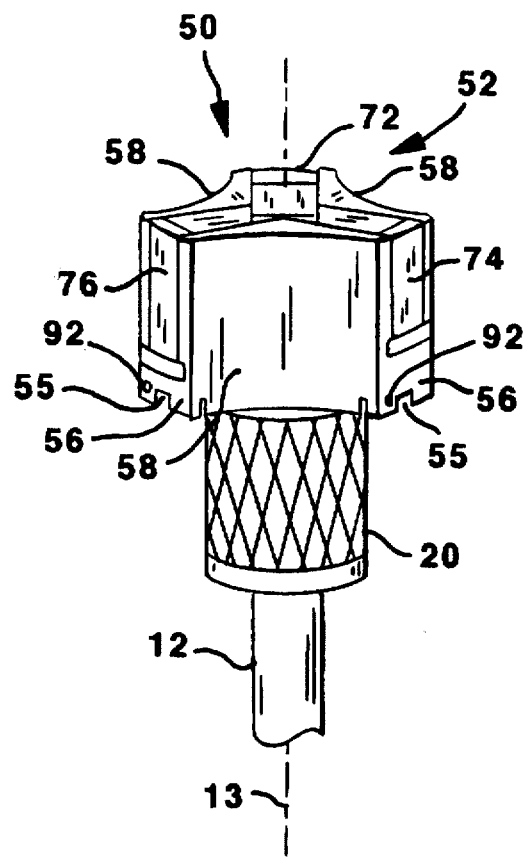
FIG. 10 is a perspective view of the holder assembly from the holder of FIG. 6 with its distally-projecting fingers moved inwardly toward the longitudinal axis of the holder.
Figure 11:
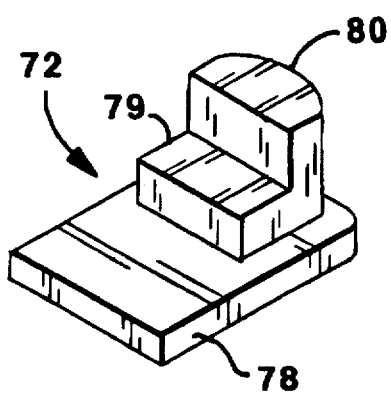
FIGS. 11 and 11A are enlarged perspective views of engaging members in the holder assembly from FIG. 10.

As noted above, each engaging member 72, 74, 76 is slidable within its associated channel 60, 62, 64, respectively. In particular, engaging members 72, 74, and 76 are slidable in the directions indicated by arrows 84 in FIG. 9. When engaging members are moved in the direction of arrows 84, their finger portions 80 move from a first radial distance away from longitudinal axis 13 of holder 50 to a second radial distance, shorter than the first, from longitudinal axis 13. FIG. 10 shows engaging members 72, 74, 76 having been moved to this second position. As also previously noted, detents 82 on each engaging member 72, 74, 76 and grooves 70 in each channel 60, 62, 64 cooperate to resist sliding of engaging members 72, 74, and 76 in the opposite direction than that indicated by arrows 84.

The manner in which holder 50 in accordance with the embodiment of FIGS. 6–12 operates to facilitate implantation of a prosthetic valve will be perhaps best appreciated with reference to FIGS. 13 and 14, which depict holder 50 in relation to prosthetic valve 36 previously described with reference to FIGS. 3 and 4.

In FIG. 13, holder 50 is shown with valve 36 having been detachably coupled thereto. In particular, a suture 90 is used to couple commissure posts 38 to finger portions 80 of engaging members 72, 74, and 76. Holes 92 may be provided in facets 56 to facilitate this suturing. As with the embodiment of the invention previously described with reference to FIGS. 1–5, suture 90 is preferably a single thread which is affixed to holder 50 in such a way that when suture 90 is cut and holder 50 withdrawn from the implant site, suture 90 is automatically retracted from valve 36. Valve 36 is placed in holder 50 such that each commissure post 38 lies adjacent one of the fingers 80. In this embodiment one continuous suture 90 extends through hole 92 and along a suture slot 93 positioned at the bottom of each facet 56. Suture 90 is run from slot 93 up to the valve where it is stitched in several places under sewing ring 42. Suture 90 is then brought back down to the suture slot 93 of the next facet 56. Suture 90 is tied off at each facet 56 through hole 92 in each facet 56. Suture 90 is exposed at each facet 56 through a channel 55 which allows the surgeon to cut the suture at each channel 55 to remove the valve from the holder.

Once valve 36 has been coupled to holder 50 as shown in FIG. 13, engaging members 72, 74, 76 are pressed inwardly toward longitudinal axis 13. This causes fingers 80 to move radially inwardly resulting in a corresponding inward deflection of commissure posts 38, as shown in FIG. 14. Engaging members are retained in the position shown in FIG. 13 due to the cooperation of detents 82 and grooves 70, as previously described. Thus, commissure posts 38 remain deflected, thereby improving the implanting surgeon's access to suture ring 42 during implant as with the previously disclosed embodiment of the invention described with reference to FIGS. 1–5.

After valve 36 has been sutured in place or at such earlier time that the surgeon desires, suture 90 is cut at channels 55 to release valve 36 from holder 50. Upon release from holder 50, commissure posts 38 of valve 36 return to their undeflected positions.

From the foregoing detailed description of particular embodiments of the invention, it should be apparent that a holder for facilitating implantation of bioprosthetic valves has been disclosed, the holder functioning to securely engage the valve and to deflect its commissure posts to improve surgical access to the valve's suture ring.

Although particular embodiments of the invention have been described herein in some detail, it is to be understood that this has been done solely for the purpose of illustrating the invention in various of its aspects, and is not intended to be limiting with respect to the scope of the invention. It is contemplated that various substitutions, alterations, and/or modifications, including but not limited to those specifically discussed herein, can be made to the disclosed embodiments of the invention without departing from the spirit and scope of the invention as defined in the appended claims, which follow.

What is claimed is:

1. A holder for a prosthetic valve having a stent defining a generally circular base thereof and three commissure posts projecting generally normally with respect to the periphery of the base, the holder comprising:

an elongate rigid handle having proximal and distal ends, the handle defining a longitudinal axis of the holder;

a main housing having a base, the main housing coupled at the main housing base to the distal end of the handle, the main housing having three sides each having a slot formed therein, the slots oriented radially with respect to the longitudinal axis;

three commissure post engaging members, each associated with a different one of the slots in the main housing, each commissure post engaging member having a base portion slidably engaged in its associated slot and a finger portion oriented perpendicularly with respect to the base portion and in parallel with respect to the longitudinal axis, the commissure post engaging members each slidable from a first position wherein the respective finger portions are each a first distance from the longitudinal axis, to a second position wherein the finger portions are a second distance, shorter than the first distance, to the longitudinal axis;

the fingers each adapted to detachably engage one of the prosthetic valve commissure posts such that when the commissure post engaging members slide from the first position to the second position for deflecting the posts inwardly to facilitate implantation of the valve.

2. A prosthetic valve holder in accordance with claim 1, wherein the base portions of the commissure post engaging members have at least one detent on a surface thereof, and wherein the slots each have at least one groove therein for engaging the at least one detent, such that the commissure post engaging members are prevented from moving from the second position to the first position.

3. A method for positioning a prosthetic valve in a heart, the prosthetic valve having a stent defining a generally circular base thereof, the base having a periphery, the stent having a plurality of commissure posts projecting generally normally with respect to the periphery of the base, the method comprising the steps of:

providing a plurality of inwardly movable fingers, each of the fingers disposed around an outer periphery of a main body, each of the fingers attached to an elongated handle at a distal end of the handle;

grasping each commissure posts of the stent with one of the fingers, each of the fingers grasping a corresponding commissure post with inwardly directed pressure;

deflecting the commissure posts inwardly by pressure applied by the fingers;

placing the valve in a desired position in a patient's heart by grasping and manipulating a proximal end of the handle;

whereby the valve is securely held by the fingers and the commissure posts are moved out of a surgeon's access path to the valve base.

4. A holder for a prosthetic valve having a stent defining a generally circular base thereof and a plurality of commissure posts projecting generally normally from the periphery of the base, the valve having a longitudinal axis normal to and centrally located to the circular base, the commissure posts extending from the periphery of the base at a peripheral distance from the longitudinal axis of the valve, the holder comprising:

an elongate rigid handle having proximal and distal ends, the handle defining a longitudinal axis of the holder;

a main housing having a base, the main housing coupled at its base to the distal end of the handle, the main housing having a plurality of slots formed therein, the number of slots corresponding to the number of commissure posts of the valve, the slots oriented substantially radially with respect to the longitudinal axis of the holder;

a plurality of commissure post engaging members, the number of commissure post engaging members being equal to the number of commissure posts, each commissure post engaging member associated with a different one of the slots in the main housing, each commissure post engaging member having a base portion slidably engaged in a slot in the main housing and a finger portion oriented substantially perpendicularly with respect to the base portion and substantially parallel to the longitudinal axis of the holder, the commissure post engaging members each slidable from a first position wherein the respective finger portions are each a first distance from the longitudinal axis of the holder to a second position wherein the finger portions are at a second distance, shorter than the first distance, from the longitudinal axis of the holder;

the finger portions each adapted to detachably engage one of the prosthetic valve commissure posts;

whereby, the finger portions in the first position are at a radial distance from the longitudinal axis of the holder equal to or greater than the peripheral distance from the longitudinal axis of the valve that the commissure posts are located; and whereby the commissure post engaging members slide from the first position to the second position and thereby deflect the commissure posts inwardly to facilitate implantation of the valve.

* * * * *